United States Patent [19]

Nomura

[11] Patent Number: 5,481,015

[45] Date of Patent: Jan. 2, 1996

[54] METHOD FOR PREPARATION OF SILOXANYL PHOSPHATE

[75] Inventor: Toshihiko Nomura, Chiba, Japan

[73] Assignee: Dow Corning Toray Silicone Co., Ltd., Tokyo, Japan

[21] Appl. No.: 369,206

[22] Filed: Jan. 5, 1995

[30] Foreign Application Priority Data

Jan. 27, 1994 [JP] Japan ................................ 6-024778

[51] Int. Cl.$^6$ ................................................. C07F 7/08
[52] U.S. Cl. ............................................................ 556/405
[58] Field of Search ............................................ 556/405

[56] References Cited

U.S. PATENT DOCUMENTS

| | | | |
|---|---|---|---|
| 3,385,822 | 5/1968 | Brown | 556/405 X |
| 3,631,088 | 12/1971 | Lengnick | 556/405 |
| 3,849,462 | 11/1974 | Lengnick | 556/405 |
| 4,125,551 | 11/1978 | Peterson | 260/448.2 E |
| 4,177,200 | 12/1979 | Razzano et al. | 260/448.2 N |
| 5,041,586 | 8/1991 | Beck et al. | 556/405 |
| 5,099,051 | 3/1992 | Beck et al. | 556/401 |

*Primary Examiner*—Paul F. Shaver
*Attorney, Agent, or Firm*—William F. Boley

[57] ABSTRACT

A method for producing siloxanyl phosphate under moderate conditions and at a fast rate to produce a high viscosity siloxanyl phosphate having a low phosphoric acid content. The siloxanyl phosphate prepared by the present method is particularly useful as an agent for neutralizing basic catalysts used in manufacturing processes for producing high viscosity diorganopolysiloxanes. The method comprises reacting a mixture comprising phosphoric acid and a hydroxyl-ended diorganosiloxane. A preferred method comprises reacting a mixture comprising phosphoric acid, a hydroxyl-ended diorganosiloxane, and a triorganosiloxy-ended diorganosiloxane.

16 Claims, No Drawings

METHOD FOR PREPARATION OF SILOXANYL PHOSPHATE

BACKGROUND OF INVENTION

This invention relates to a method of manufacturing siloxanyl phosphate, and specifically, it relates to a method for producing siloxanyl phosphate under moderate conditions at a fast rate, to produce a siloxanyl phosphate which is of high viscosity and of low phosphoric acid content and which can be used as a neutralization agent for the basic catalyst used in manufacturing processes for high viscosity diorganopolysiloxanes.

The ring-opening polymerization of cyclic diorganopolysiloxanes catalyzed by a basic catalyst, namely, alkali metal hydroxide such as sodium hydroxide, potassium hydroxide, cesium hydroxide, lithium hydroxide, etc., or silanolates or siloxanates of these alkali metals, or the condensation polymerization of α,ω-hydroxyl-capped diorganopolysiloxane by the above basic catalyst, followed by the neutralization of the basic catalyst by acidic substances are well known methods for manufacturing high viscosity diorganopolysiloxanes. In general, the acidic substance used as the neutralization agent for the above basic catalyst can be specifically, hydrochloric acid, acetic acid, phosphoric acid, carbon dioxide, etc. However, the hydrochloric acid and acetic acid added have to be weighed out exactly to their theoretical quantity against the basic catalyst in the diorganopolysiloxane, because the heat resistance of the diorganopolysiloxane obtained is degraded by excess basic catalyst or by excess acidic substance. Also, when carbon dioxide, which is a weak acid, is used, the neutralization salt produced by the neutralization of the basic catalyst in the diorganopolysiloxane decomposes at elevated temperatures and forms a basic substance again. Therefore, this neutralization salt has to be removed completely from the diorganopolysiloxane, or otherwise the heat resistance of the diorganopolysiloxane obtained is generally poor.

Phosphoric acid is a preferable neutralization agent in that the phosphate produced by neutralization with the basic catalyst in the diorganopolysiloxane functions as a buffer for the residual phosphoric acid or basic catalyst even if its addition amount is not weighed out exactly to the theoretical quantity against the basic catalyst in the diorganopolysiloxane, and therefore suppresses the heat resistance degradation of the diorganopolysiloxane. However, phosphoric acid is, similarly to other acidic substances such as hydrochloric acid, acetic acid, etc., insoluble in diorganopolysiloxane, and therefore, its mixing and contacting efficiency during the neutralization process is low, and it has been a problem that its neutralization time is too long.

Because of this situation, phosphoric acid-containing organic silicon compounds such as silylphosphate, siloxanyl phosphate, etc. have been studied as the neutralization agent for the basic catalyst in diorganopolysiloxanes. In particular, siloxanyl phosphate is of merit since its viscosity is higher compared to silylphosphate. Therefore, the neutralization time can be shortened drastically by the improved miscibility with the diorganopolysiloxane when it is used as the neutralization agent of the basic catalyst in the manufacturing process of the high viscosity diorganopolysiloxane using the above basic catalyst. Also, siloxanyl phosphate is of merit since its phosphoric acid content in a molecule is less than that of silylphosphate, and even if it is not weighed out correctly to its theoretical quantity against the basic catalyst, this error in the theoretical quantity against the above basic catalyst can be smaller.

Manufacturing methods for siloxanyl phosphates which have such merits is illustrated, for example, by a method of manufacturing siloxanyl phosphate where phosphoric acid or a phosphorus halide compound and hexaorganodisiloxane and triorganosiloxy-capped diorganopolysiloxane are heated to react while removing generated water (refer to JP (Kokai) 54-89000). A method of manufacturing siloxanyl phosphate is taught where phosphoric acid and triorganosiloxy-capped diorganopolysiloxane are reacted in the presence of silylphosphate catalyst (refer to JP (Kokai) 54-109924). A method of manufacturing siloxanyl phosphate is taught where a silylphosphate mixture, which is prepared by adding phosphoric acid to hexaorganodisiloxane under heated reflux and heating while removing generated water, and cyclic diorganosiloxane are reacted (refer to JP (Kokai) 5-194557).

However, according to the manufacturing methods of siloxanyl phosphate proposed in the above patent journals, the reaction rate is slow without increased amount of phosphoric acid addition in the reaction system. Also, the reaction has to proceed at high temperatures in the range of 150° C.–200° C. for several hours since the reaction of siloxanyl phosphate is extremely slow under moderate conditions. Consequently, it has been a problem that the phosphoric acid content in the siloxanyl phosphate thus obtained is naturally greater. Furthermore, according to the manufacturing methods proposed in JP (Kokai) 54-109924 and JP (Kokai) 5-194557, the reaction does not proceed at all without silylphosphate. Therefore, it is necessary to prepare silylphosphate beforehand, and this creates a problem in that the manufacturing process for siloxanyl phosphate becomes complex.

The objective of the present invention is to provide a manufacturing method for a high viscosity and low phosphoric acid content siloxanyl phosphate, which can be used as neutralization agent for the basic catalyst used in a manufacturing process for high viscosity diorganopolysiloxanes and which can neutralize the basic catalyst quickly under moderate conditions.

SUMMARY OF INVENTION

This invention relates to a method for producing siloxanyl phosphate under moderate conditions and at a fast rate to produce a high viscosity siloxanyl phosphate having a low phosphoric acid content. The siloxanyl phosphate prepared by the present method is particularly useful as an agent for neutralizing basic catalysts used in manufacturing process for producing high viscosity diorganopolysiloxanes. The method comprises reacting a mixture comprising phosphoric acid and a hydroxyl-ended diorganosiloxane. A preferred method comprises reacting a mixture comprising phosphoric acid, a hydroxyl-ended diorganosiloxane, and a triorganosiloxy-ended diorganosiloxane.

DESCRIPTION OF INVENTION

The present invention is a method for preparing siloxanyl phosphates described by formula:

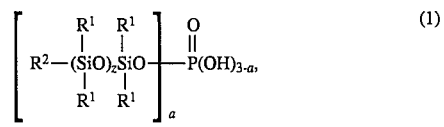

where each $R^1$ is an independently selected monovalent hydrocarbon group, $R^2$ is a hydroxyl group or monovalent hydrocarbon group where at least one of $R^2$ is a hydroxyl group, z is an integer of 1 or greater, and a is an integer of 1 to 3. The method comprises reacting a mixture comprising:

(A) phosphoric acid and
(B) a hydroxyl-ended diorganosiloxane described by formula:

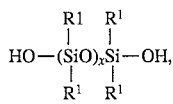
(2)

where each $R^1$ is an independently selected monovalent hydrocarbon group, and x is an integer of 1 or greater.

The mixture comprising the phosphoric acid and hydroxyl-ended diorganosiloxane may also comprise as needed (C) a triorganosiloxy-ended diorganosiloxane described by formula:

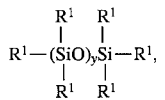
(3)

where each $R^1$ is an independently selected monovalent hydrocarbon group, and y is an integer of 1 or greater.

The method of producing siloxanyl phosphate by the present invention is explained in detail in the following.

The constituent (A), phosphoric acid, is the major raw material in the method of the present invention, and its purity is not particularly limited, and also, if it is used as an aqueous phosphoric acid solution, its concentration is not limited. In general, commercially available aqueous phosphoric acid solution (about 85 weight %) can be used as the phosphoric acid of the constituent (A).

The constituent (B), hydroxyl-ended diorganosiloxane, is the raw material which can be prepared into the intended siloxanyl phosphate in the present method by forming P—O—Si bonds in a fast reaction under moderate conditions by reaction with constituent (A). Constituent (B) is described by formula (2). In formula (2), each $R^1$ is an independently selected monovalent hydrocarbon group, and specifically it can be an alkyl group such as methyl, ethyl, propyl, butyl, pentyl, hexyl, heptyl, octyl, etc.; an alkenyl group such as vinyl, allyl, butenyl, pentenyl, hexenyl, heptenyl, octenyl, etc.; an aryl group such as phenyl, tolyl, xylyl, naphthyl, etc.; an aralkyl group such as benzyl, phenethyl, etc.; or a halogen substituted alkyl group such as 3-chloropropyl, 3,3,3-trifluoropropyl, etc. Preferred is when $R^1$ is a methyl group or a phenyl group. Also, in the above formula (2), x is an integer of 1 or greater, and preferably an integer in the range of 1 to 100.

Specific examples of constituent (b) include 1,3-dihydroxy- 1,1,3,3-tetramethyldisiloxane, 1,5-dihydroxy-1,1,3, 3,5,5-hexamethyltrisiloxane, α,ω-hydroxydimethylsiloxy-capped dimethylpolysiloxane, α,ω-hydroxydimethylsiloxy-capped methylphenylpolysiloxane, α,ω-hydroxydimethylsiloxy-capped dimethylsiloxane-methylphenylsiloxane copolymer, α,ω-hydroxydimethylsiloxy-capped methylvinylpolysiloxane, α,ω-hydroxydimethylsiloxy-capped dimethylsiloxane-methylvinylsiloxane copolymer, α,ω-hydroxydimethylsiloxy-capped methylphenylsiloxanediphenylsiloxane copolymer, and α,ω-hydroxydimethylsiloxy-capped methylvinylpolysiloxane.

The method of preparation of constituent (B), is not particularly limited, and for example, it can be a method in which, after a hydrolyzable silane such as diorganodichlorosilane, diorganodialkoxysilane, etc. is hydrolyzed, it is subjected to a condensation reaction; a method in which, after a cyclic diorganosiloxane is subjected to a polymerization reaction with a basic catalyst, the basic catalyst is neutralized by acetic acid, hydrochloric acid, or carbon dioxide; or a method in which, after cyclic diorganosiloxane is subjected to a polymerization reaction with an acidic catalyst, the acidic catalyst is neutralized by sodium hydroxide, potassium hydroxide, or ammonia gas.

Furthermore in the present method the constituent (C), trimethylsiloxy-ended diorganosiloxane, can be reacted, as needed, together with constituent (B). Constituent (C) is described by formula (3). It is preferable to use the constituent (C) in the present method since the viscosity of the siloxanyl phosphate obtained can be readily adjusted compared to the situation when only constituent (A) is reacted with constituent (B). In formula (3), each $R^1$ is an independently selected monovalent hydrocarbon group. $R^1$ can be specifically, an alkyl group such as methyl, ethyl, propyl, butyl, pentyl, hexyl, heptyl, octyl, etc.; an alkenyl group such as vinyl, allyl, butenyl, pentenyl, hexenyl, heptenyl, octenyl, etc.; an aryl group such as phenyl, tolyl, xylyl, naphthyl, etc.; an aralkyl group such as benzyl group, phenethyl, etc.; or a halogen substituted alkyl group such as 3-chloropropyl, 3,3,3-trifluoropropyl, etc. Preferred is when in formula (3) $R^1$ is a methyl group or a phenyl group. Also, in formula (3), y is an integer of 1 or greater, and preferably an integer in the range of 1 to 100.

Specific examples of constituent (C) include 1,1,1,3,3,3-hexamethyldisiloxane, 1,1,3,3-tetramethyl-1,3-divinyldisiloxane, 1,1,3,3-tetramethyl-1,3-diphenylsiloxane, 1,1,1,3,3, 5,5,5-octamethyltrisiloxane, α,ω-trimethylsiloxy-capped dimethylpolysiloxane, α,ω-trimethylsiloxy-capped methylvinylpolysiloxane, α,ω-trimethylsiloxy-capped methylphenylpolysiloxane, α,ω-trimethylsiloxy-capped dimethylsiloxane-methylphenylsiloxane copolymer, α,ω-trimethylsiloxy-capped dimethylsiloxane-methylvinylsiloxane copolymer, α,ω-trimethylsiloxy-capped methylphenylsiloxane-diphenylsiloxane copolymer, α,ω-dimethylvinylsiloxy-capped dimethylpolysiloxane, α,ω-dimethylvinylsiloxy-capped methylphenylpolysiloxane, α,ω-dimethylvinylsiloxy-capped methylvinylpolysiloxane, α,ω-dimethylvinylsiloxy-capped dimethylsiloxane-methylphenylsiloxane copolymer, α,ω-dimethylvinylsiloxy-capped dimethylsiloxane-methylvinylsiloxane copolymer, α,ω-dimethylvinylsiloxy-capped methylphenylsiloxanediphenylsiloxane copolymer, α,ω-dimethylphenylsiloxy-capped dimethylpolysiloxane, α,ω-dimethylphenylsiloxy-capped methylphenylpolysiloxane, α,ω-dimethylphenylsiloxy-capped methylvinylpolysiloxane, α,ω-dimethylphenylsiloxy-capped dimethylsiloxane-methylphenylsiloxane copolymer, α,ω-dimethylphenylsiloxy-capped dimethylsiloxane-methylvinylsiloxane copolymer, and α,ω-dimethylphenylsiloxy-capped methylphenylsiloxane-diphenylsiloxane copolymer.

There is no particular limitation for the preparation method of such constituent (C), and for example, it can be a method in which hydrolyzable triorganosilane such as triorganochlorosilane, triorganoalkoxysilane, etc., together with diorganodichlorosilane or diorganodialkoxysilane as needed, is subjected to a hydrolytic condensation reaction; a method in which, after the polymerization reaction of hexaorganodisiloxane and cyclic diorganosiloxane with basic catalyst, the basic catalyst is neutralized; a method in which, after the polymerization reaction of hexaorganodisiloxane and cyclic diorganosiloxane with acidic catalyst, the acidic catalyst is neutralized; and a method in which the above constituent (B), hydroxyl-ended diorganosiloxane, is reacted with triorganochlorosilane or hexaorganodisilazane and capped with triorganosiloxy groups at the terminals of the molecule.

Furthermore, in the present method, cyclic diorganosiloxane described by formula:

can be added to the method in order to increase the siloxane units in the siloxanyl phosphate obtained and, in addition, in order to manufacture high viscosity siloxanyl phosphate. In the above formula, each $R^1$ is an independently selected monovalent hydrocarbon group and can be an alkyl group such as methyl, ethyl, propyl, butyl, pentyl, hexyl, heptyl, octyl, etc.; an alkenyl group such as vinyl, allyl, butenyl, pentenyl, hexenyl, heptenyl, octenyl, etc.; an aryl group such as phenyl, tolyl, xylyl, naphthyl, etc.; an aralkyl group such as benzyl, phenethyl, etc.; or a halogen substituted alkyl group such as 3-chloropropyl, 3,3,3-trifluoropropyl, etc. Preferred is where the $R^1$ groups of formula (4) are a methyl group or a phenyl group. Also in formula (4), p is an integer of 4 or greater.

Specific examples of cyclic diorganosiloxane include 1,1,3,3,5,5,7,7-octamethyltetracyclosiloxane, 1,3,5,7-tetramethyl- 1,3,5,7-tetravinyltetracyclosiloxane, 1,3,5,7-tetramethyl- 1,3,5,7-tetraphenyltetracyclosiloxane, 1,1,3,3,5,5,7,7,9,9-decamethylpentacyclosiloxane, 1,3,5,7,9-pentamethyl- 1,3,5,7,9-pentavinylpentacyclosiloxane, and 1,3,5,7,9-pentamethyl-1,3,5,7,9-pentaphenylpentacyclosiloxane.

In the present method, the reaction conditions are not particularly limited, and the preferable reaction temperature is in a range from room temperature to 200° C., and more preferably in a range of 80 to 150° C. Also, the reaction time varies depending on the reaction temperature, but preferably is in the range of several tens of minutes to several hours.

In the present method, it is preferable to remove water from the reaction and condensation water generated during the reaction from the process. The method to remove water from the process can be, for example, azeotropic removal by organic solvent, or removal by heating under atmospheric pressure or reduced pressure. Also, the storage stability of the siloxanyl phosphate prepared in this manner can be improved by storing in sealed containers to avoid moisture.

In the present method, when the constituent (A) and the constituent (B) and also, as needed, the constituent (C) are reacted, organic solvent can be added to the reaction. As long as the above reaction is not impaired, there is no particular limitation on the organic solvent which can be used, and specifically, it can be an aromatic organic solvent such as toluene, xylene, etc.; an aliphatic hydrocarbon organic solvent such as heptane, hexane, octane, etc.; a cyclic aliphatic hydrocarbon organic solvent such as cyclohexane, cycloheptane, etc.; a ketone organic solvent such as acetone, methylethylketone, methylisobutylketone, etc.; an ester organic solvent such as methyl acetate, ethyl acetate, isobutyl acetate, etc.; and other organic solvents such as tetrahydrofuran, dimethylformamide, and dimethyl sulfoxide.

The siloxanyl phosphate prepared by the present method are described by formula (1). In formula (1), $R^1$ is a monovalent hydrocarbon group, and specifically $R^1$ can be an alkyl group such as methyl, ethyl, propyl, butyl, pentyl, hexyl, heptyl, octyl, etc.; an alkenyl group such as vinyl, allyl, butenyl, pentenyl, hexenyl, heptenyl, octenyl, etc.; an aryl group such as phenyl, tolyl, xylyl, naphthyl, etc.; an aralkyl group such as benzyl, phenethyl, etc.; or a halogen substituted alkyl group such as 3-chloropropyl, 3,3,3-trifluoropropyl, etc. Preferred is where the $R^1$ of formula (1) is a methyl group or a phenyl group. Also in the above formula, $R^2$ is a hydroxyl group or a monovalent hydrocarbon group, and at least one of $R^2$ is a hydroxyl group. Specific examples of $R^2$ can be the same groups as described for $R^1$. Preferred is where $R^2$ is a hydroxyl group, a methyl group, or a phenyl group. Also, in the above formula (1), z is an integer of 1 or greater, and a is an integer of 1 to 3. Such siloxanyl phosphates are obtained from the present method as a mixture, and the major constituents of the siloxanyl phosphate mixture are described by formulas:

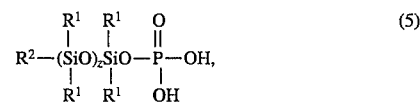

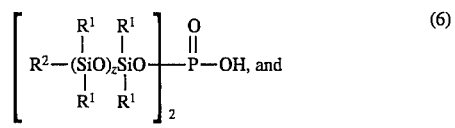

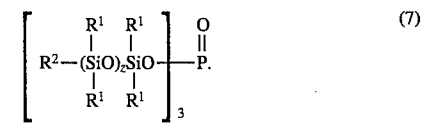

In formulas (5), (6), and (7) each $R^1$ is an independently selected monovalent hydrocarbon group as previously described, each $R^2$ is an independently selected monovalent hydrocarbon group as previously described or a hydroxyl group, and z is an integer of 1 or greater.

In addition to the siloxanyl phosphates described by the above formulas, also formed are siloxanyl phosphates having a structure where two phosphorus atoms are bonded by a diorganosiloxane chain, described, for example, by formula:

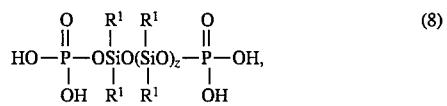

where $R^1$ is a monovalent hydrocarbon group as previously described, and z is an integer of 1 or greater. Each of the siloxanyl phosphates comprising the product mixture of the present method does not have to be isolated and purified. The product mixture can be used as the neutralization agent for the basic catalyst in a manufacturing process for a high viscosity diorganopolysiloxane.

The viscosity of the siloxanyl phosphate prepared by the present method is not particularly limited, and preferably is in a range of from several tens of centipoises to several tens of thousand centipoises. A siloxanyl phosphate of an appropriate viscosity can be used depending on its application and handling method. Also, the phosphoric acid content of the siloxanyl phosphate prepared by the method of the present invention is not particularly limited, and preferably is in a range of 0.01 to 10 weight %. A siloxanyl phosphate of an appropriate phosphoric acid content can be used depending on its application and handling method. Since the siloxanyl phosphate prepared by the present method is of high viscosity and low phosphoric acid content, when it is used as a neutralization agent for the basic catalyst in a manufacturing process for high viscosity diorganopolysiloxane, it can be mixed with this diorganopolysiloxane quickly, and the basic catalyst can be neutralized in a short time. Therefore, the siloxanyl phosphate prepared by the present method is suitable as a neutralization agent in a manufacturing process for diorganopolysiloxanes having a viscosity of 1000 centipoises at 25° C. to diorganopolysiloxane gums of high viscosity. In order to neutralize the basic catalyst with the siloxanyl phosphate produced by the present method, the phosphoric acid in the siloxanyl phosphate should be preferably more than the equivalent amount of the basic catalyst. For example, when potassium catalyst is used as the basic catalyst, phosphoric acid content of the siloxanyl phosphate is preferably in a range of 0.5 to 1 mole per mole of potassium.

The present method for preparing siloxanyl phosphate is explained in detail by the following Examples. In the Examples, the viscosity is the value measured at 25° C.

EXAMPLE 1

2.96 g of a 85 weight % aqueous solution of phosphoric acid and 397.0 g of α,ω-hydroxydimethylsiloxy-capped dimethylpolysiloxane described by the average formula:

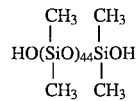

were loaded in a 1 liter round-bottom flask equipped with a Dean-Stark trap, thermometer, and stirrer, and heated and stirred at 80° C. for 6 hours. Then the viscosity of the system increased and generation of condensation water was observed, and a clear and viscous liquid having a viscosity of 824,000 centipoises was obtained.

This viscous liquid was analyzed by $^{29}$Si-nuclear magnetic resonance spectra (hereafter NMR) and $^{31}$P-NMR. No absorption attributable to O=P(OH)$_3$ was observed, whereas O=P(OH)$_2$ (OSi) bonding, O=P(OH) (OSi)$_2$ bonding, and O=P(OSi)$_3$ bonding were identified and the mole ratio of each bonding was 6.5: 81.5: 12.0. The viscous liquid was identified as a dimethylsiloxanyl phosphate mixture (phosphoric acid content=0.63 weight %) of which the major constituents were dimethylsiloxanyl phosphate described by the average formula:

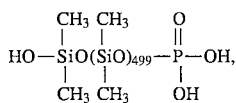

dimethylsiloxanyl phosphate described by the average formula

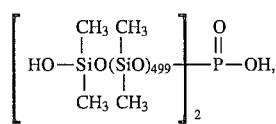

and dimethylsiloxanyl phosphate described by the average formula

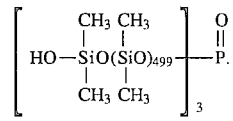

EXAMPLE 2

2.96 g of a 85 weight % aqueous solution of phosphoric acid and 397.0 g of α,ω-hydroxydimethylsiloxy-capped dimethylpolysiloxane described by the average formula

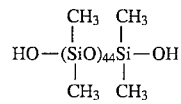

were loaded in a 1 liter round-bottom flask equipped with a Dean-Stark trap, thermometer, and stirrer, and heated and stirred at 80° C. for 6 hours. Then the viscosity of the system increased and generation of condensation water was observed. Subsequently to this system, 22.15 g of α,ω-trimethylsiloxy-capped dimethylpolysiloxane described by the average formula

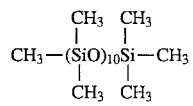

was added and heated and stirred at 90° C. for 5 hours. Then, this system was heated and stirred at 140° C. to remove condensation water out of the system, and a clear viscous liquid with a viscosity of 3,000 centipoises was obtained.

This viscous liquid was analyzed by $^{29}$Si-NMR and $^{31}$P-NMR. No absorption attributable to O=P(OH)$_3$ was observed, whereas O=P(OH) (OSi)$_2$ bonding and O=P(OSi)$_3$ bonding were identified and the mole ratio of each bonding was 78.0: 22.0. The viscous liquid was was identified as a dimethylsiloxanyl phosphate mixture (phosphoric acid content=0.60 weight %) of which the major constituents were dimethylsmloxanyl phosphate described by the average formula

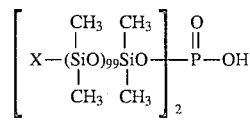

and dimethylsiloxanyl phosphate described by the average formula

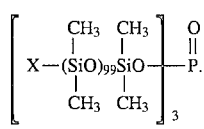

In the above formulas, X is hydroxyl groups and methyl groups.

EXAMPLE 3

3.0 g of a 85 weight % aqueous solution of phosphoric acid, 350.0 g of α,ω-hydroxydimethylsiloxy-capped dimethylpolysiloxane described by the average formula

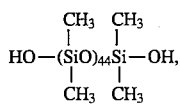

and 50.0 g of α,ω-trimethylsiloxy-capped dimethylpolysiloxane described by the average formula

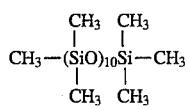

were loaded in a 1 liter round-bottom flask equipped with a Dean-Stark trap, thermometer, and stirrer, and heated and stirred at 140° C. for 4 hours. Then the viscosity of the system increased and generation of condensation water was observed, and a clear viscous liquid with a viscosity of 440 centipoises was obtained.

This viscous liquid was analyzed by $^{29}$Si-NMR and $^{31}$P-NMR. No absorption attributable to O=P(OH)$_3$ was observed, whereas O=P(OH) (OSi)$_2$ bonding and O=P(OSi)$_3$ bonding were identified and the mole ratio of each bonding was 80.0: 20.0. The viscous liquid was identified as a dimethylsiloxanyl phosphate mixture (phosphoric acid content=0.63 weight %) of which the major constituents were dimethylsiloxanyl phosphate described by the average formula

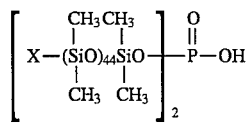

and dimethylsiloxanyl phosphate described by the average formula

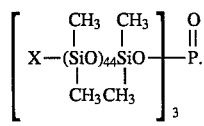

In the above formulas, X is hydroxyl groups and methyl groups.

Comparison example 1. 2.45 g of a 85 weight % aqueous solution of phosphoric acid, 50.0 g of α,ω-trimethylsiloxy-capped dimethylpolysiloxane described by the average formula

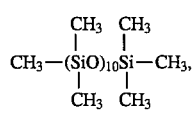

and 47.5 g of 1,1,3,3,5,5,7,7-octamethyltetracyclosiloxane were loaded in a 1 liter round-bottom flask equipped with a Dean-Stark trap, thermometer, and stirrer, and heated and stirred at 100° C. for 6 hours. No equilibrium polymer was obtained.

Comparison example 2. 2.72 g of a 85 weight % aqueous solution of phosphoric acid and 397.7 g of α,ω-trimethylsiloxy-capped dimethylpolysiloxane described by average formula

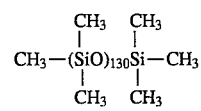

were loaded in a 1 liter round-bottom flask equipped with a Dean-Stark trap, thermometer, and stirrer, and heated and stirred at 90° C. for 6 hours. No equilibrium polymer was obtained.

Comparison example 3. 30.0 g dimethylsiloxanyl phosphate catalyst (phosphoric acid content=0.63 weight %), of which the major constituent was dimethylsiloxanyl phosphate described by the average formula

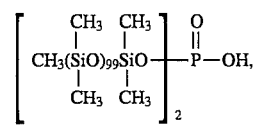

3.0 g of a 85 weight % aqueous solution of phosphoric acid, 50.0 g α,ω-trimethylsiloxy-capped dimethylpolysiloxane described by the average formula

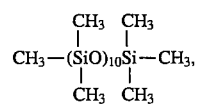

and 350.0 g of 1,1,3,3,5,5,7,7-octamethyltetracyclosiloxane were loaded in a 1 liter round-bottom flask equipped with a Dean-Stark trap, thermometer, and stirrer, and heated and stirred at 150° C. for 6 hours. No equilibrium polymer was obtained.

Application example. Cyclic dimethylsiloxane, of which the major constituent is 1,1,3,3,5,5,7,7-octamethyltetracyclosiloxane, and 1,1,3,3-tetramethyl-1,3-divinylsiloxane, and potassium hydroxide in the amount of 100 ppm were loaded in a small Ross mixer, and heated and stirred at 150° C. for polymerization. Subsequently, dimethylsiloxanyl phosphate mixture as prepared in Example 2 (phosphoric acid content=0.60 weight %) was added to this system in the amount of 1 mole of potassium per 0.7 mole of phosphorus in the above and stirred for 10 minutes. In this manner, α,ω-dimethylvinylsiloxy-capped dimethylpolysiloxane with a viscosity of 10,000 centipoises was prepared. This dimethylpolysiloxane was analyzed by thermogravimetric analysis (hereafter TGA), and it was found that the temperature at which 10 % weight loss occurred was 470° C.

Also in the above polymerization, neutralization was performed using trimethylsilyl phosphate instead of dimethylsiloxanyl phosphate mixture as prepared in Example 2. By the TGA analysis of α,ω-dimethylvinylsiloxy-capped dimethylpolysiloxane obtained in this manner, it was found that the temperature at which 10% weight loss occurred was 370° C.

Also in the above polymerization, the TGA analysis of α,ω-dimethylvinylsiloxy-capped dimethylpolysiloxane obtained by neutralization using trimethylsilyl phosphate and stirring for 2 hours showed that the temperature at which 10% weight loss occurred was 470° C.

Further in the above polymerization, the TGA analysis of α,ω-dimethylvinylsiloxy-capped dimethylpolysiloxane obtained by neutralization by introducing carbon dioxide gas into the system and stirring for 2 hours showed that the temperature at which 10 % weight loss occurred was 320° C.

We claim:

1. A method for preparing siloxanyl phosphates described by formula

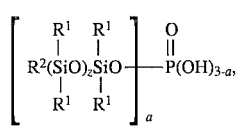

where each $R^1$ is an independently selected monovalent hydrocarbon group, $R^2$ is a hydroxyl group or monovalent hydrocarbon group and at least one $R^2$ is a hydroxyl group, z is an integer of 1 or greater, and a is an integer of 1 to 3, the method comprising reacting a mixture comprising (A) phosphoric acid and
(B) a hydroxyl-ended diorganosiloxane described by formula

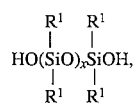

where each $R^1$ is an independently selected monovalent hydrocarbon group and x is an integer of 1 or greater.

2. A method according to claim 1, where the mixture further comprises (C) a triorganosiloxy-ended diorganosiloxane described by formula

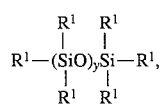

where each $R^1$ is an independently selected monovalent hydrocarbon group and y is an integer of 1 or greater.

3. A method according to claim 1, where each $R^1$ is independently selected from a group consisting of methyl and phenyl.

4. A method according to claim 1, where x is an integer in a range of 1 to 100.

5. A method according to claim 2, where each $R^1$ is independently selected from a group consisting of methyl and phenyl.

6. A method according to claim 2, where y is an integer in a range of 1 to 100.

7. A method according to claim 1, further comprising (D) a cyclic diorganosiloxane described by formula

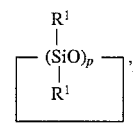

where each $R^1$ is an independently selected monovalent hydrocarbon group and p is an integer of 4 or greater.

8. A method according to claim 7, where each $R^1$ is independently selected from a group consisting of methyl and phenyl.

9. A method according to claim 1, where the mixture is reacted at a temperature within a range, from room temperature to 200° C.

10. A method according to claim 1, where the mixture is reacted at a temperature within a range of 80° C. to 150° C.

11. A method according to claim 1, further comprising (E) an organic solvent.

12. A method according to claim 1, where the siloxanyl phosphate prepared by the method has a phosphoric acid content in a range of 0.01 to 10 weight percent.

13. A method for preparing siloxanyl phosphates, the method comprising reacting a mixture comprising (A) phosphoric acid,
(B) a hydroxyl-ended diorganosiloxane described by formula

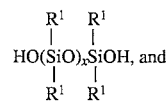

(C) a triorganosiloxy-ended diorganosiloxane described by formula

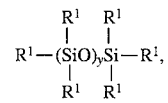

at a temperature within a range of room temperature to 200° C., where each $R^1$ is an independently selected monovalent hydrocarbon group, x is an integer of 1 to 100, and y is an integer of 1 to 100.

14. A method according to claim 13, further comprising (D) a cyclic diorganosiloxane described by formula

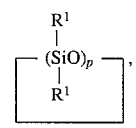

where each $R^1$ is an independently selected monovalent hydrocarbon group and p is an integer of 4 or greater.

15. A method according to claim 14, where each $R^1$ is independently selected from a group consisting of methyl and phenyl.

16. A method according to claim 15, further comprising (E) an organic solvent.

* * * * *